United States Patent
Nakakado

(12) 
(10) Patent No.: US 6,722,494 B2
(45) Date of Patent: Apr. 20, 2004

(54) METHOD AND DEVICE FOR TRANSPORTATION

(75) Inventor: Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 34 days.

(21) Appl. No.: 09/889,275

(22) PCT Filed: Dec. 14, 2000

(86) PCT No.: PCT/JP00/08879

§ 371 (c)(1),
(2), (4) Date: Jan. 8, 2002

(87) PCT Pub. No.: WO01/44086

PCT Pub. Date: Jun. 21, 2001

(65) Prior Publication Data

US 2002/0125105 A1 Sep. 12, 2002

(30) Foreign Application Priority Data

Dec. 16, 1999 (JP) .......................................... 11-357294

(51) Int. Cl.[7] .............................................. B65G 47/24
(52) U.S. Cl. ............. 198/792; 198/377.01; 198/377.02; 198/377.04; 198/377.07; 198/377.08; 198/470.1; 198/474.1
(58) Field of Search ........................... 198/792, 377.07, 198/377.08, 377.01, 377.02, 377.03, 377.04, 470.01, 474.1, 476.1

(56) References Cited

U.S. PATENT DOCUMENTS

| | | | |
|---|---|---|---|
| 4,506,779 A | 3/1985 | Seragnoli | |
| 4,610,751 A | 9/1986 | Eschler | |
| 4,617,082 A | 10/1986 | Oshefsky et al. | ............ 156/447 |
| 4,726,876 A | 2/1988 | Tomsovic | |
| 5,025,910 A | 6/1991 | Lasure et al. | |
| 5,025,916 A * | 6/1991 | Kaminski | ............... 198/803.15 |
| 5,556,504 A | 9/1996 | Rajala et al. | ............... 156/519 |
| 5,660,657 A | 8/1997 | Rajala et al. | |
| 5,927,473 A | 7/1999 | Draghetti | |
| 6,022,443 A | 2/2000 | Rajala et al. | |
| 6,109,419 A * | 8/2000 | Spatafora et al. | ...... 198/377.08 |

FOREIGN PATENT DOCUMENTS

| | | |
|---|---|---|
| EP | 439897 | 8/1991 |
| EP | 895951 | 2/1999 |
| EP | 1062929 | 12/2000 |
| JP | 63317576 | 12/1988 |
| JP | 1272803 | 10/1989 |
| JP | 8052696 | 2/1996 |
| WO | WO88/05416 | 7/1988 |
| WO | WO 01/44086 | 6/2001 |

OTHER PUBLICATIONS

EP Search Report for EP Application No. 00981733.9 dated Mar. 20, 2003.
European Search Report for European Patent Application No. 02 02 4483.6–2124.

* cited by examiner

Primary Examiner—Douglas Hess
(74) Attorney, Agent, or Firm—Renner, Otto, Boisselle & Sklar, LLP

(57) ABSTRACT

A transfer apparatus 10 includes crank arms 22 each of which is pivotally attached to a driving wheel 21, link levers 23 each of which has its one end pin-linked to the tip of the crank arm 22, and revolving sections 30 each of which is pin-linked to the other end of the link lever 23 and held at a distance from the rotation axis 210 of the driving wheel 21, wherein: the crank arm 22 is provided with a velocity-changing cam roller 223 protruding therefrom at a position spaced apart from the pivot center thereof; the velocity-changing cam roller 223 is guided while being engaged with the velocity-changing cam groove 44 which is formed to be eccentric to the rotation axis 210 of the driving wheel 21, whereby the tip of the crank arm 22 swings during one complete rotation of the driving wheel 21; and, as a result, the angular velocity of the link lever 23 linked to the tip of the crank arm 22 and the revolving section 30 periodically increases/decreases with respect to the angular velocity of the driving wheel 21.

18 Claims, 9 Drawing Sheets

METHOD AND DEVICE FOR TRANSPORTATION

TECHNICAL FIELD

The present invention relates to a transfer method for increasing or decreasing the transfer Velocity of a workpiece (including a material) when the workpiece moving on a transfer line is handed over to another transfer line, and a transfer apparatus having the accelerating/decelerating function.

BACKGROUND ART

Japanese Patent No. 2580493 discloses an apparatus for cutting sanitary goods, and increasing the transfer pitch of the cut sanitary goods. Specifically, the die cutter roll for cutting and transferring the sanitary goods hands over the sanitary goods to a transfer roll that rotates at a higher velocity than the circumferential velocity of the die cutter roll, whereby the transfer pitch of the sanitary goods on the transfer surface of the transfer roll is greater than the transfer pitch thereof on the transfer surface of the die cutter roll.

Japanese Laid-Open Patent Publication No. 63-317576 discloses a technique of cutting an elastic tape by a rotating drum, turning the cut elastic tape pieces on the rotating drum by 90° with respect to the transfer direction, and attaching the elastic tape pieces to an adherend sheet being transferred by an adherend sheet transfer apparatus. The circumferential velocity of the rotating drum is higher than the circumferential velocity of an elongation roller for feeding the elastic tape to the rotating drum, and the elastic tape, which is a continuous member, is gradually elongated while being in contact with the surface of the rotating drum, thereby increasing the interval between the cut elastic tape pieces.

Japanese Laid-Open Patent Publication No. 57-102427 discloses a transfer apparatus for transferring an elongate stick-shaped item such as a cigarette in a direction perpendicular to the axial direction thereof. This transfer apparatus holds each stick-shaped item in a housing having a semicircular cross section, and changes the transfer pitch of the stick-shaped items held on a linking conveyer, which is disposed between two conveyers, while the linking conveyer moves about halfway around.

U.S. Pat. No. 5,025,910 discloses a technique for turning a vacuum pickup shoe by 90°.

However, when transferring a soft workpiece which has a length or width such as sanitary goods, for example, by using the conventional techniques described above, the workpiece is likely to be wrinkled when it is handed over between rotating members such as rolls and drums, thereby failing to sufficiently satisfy the requirement of transferring an item stably and at a high velocity. The present invention provides a transfer method and a transfer apparatus capable of satisfying such a requirement.

DISCLOSURE OF THE INVENTION

A transfer method of the present invention is a transfer method for transferring a workpiece from a preceding stage to a subsequent stage by using a transfer apparatus including at least one transfer section capable of revolving around a rotation axis, the method including: a pickup step, wherein in order for the transfer section to pick up the workpiece transferred by the preceding stage at a first transfer velocity, the transfer section moves at a pickup velocity substantially equal to the first transfer velocity in a pickup area having a width; a velocity-changing step of changing the transfer velocity of the transfer section while the transfer section is holding the workpiece which has been picked up; and a hand-over step, wherein in order to transfer the workpiece at a second transfer velocity by the subsequent stage, the transfer section moves at a hand-over velocity substantially equal to the second transfer velocity in a hand-over area having a width, wherein the pickup velocity and the hand-over velocity are different from each other.

A transfer apparatus of the present invention is a transfer apparatus, including at least one transfer section capable of revolving around a rotation axis, and a velocity-changing section for changing a transfer velocity of the transfer section, wherein: in order for the transfer section to pick up a workpiece transferred at a first transfer velocity, the transfer section holds the workpiece while moving at a pickup velocity substantially equal to the first transfer velocity in a pickup area having a width; the velocity-changing section changes the transfer velocity of the transfer section holding the workpiece; in order to transfer the workpiece at a second transfer velocity outside the transfer apparatus, the transfer section moves at a hand-over velocity substantially equal to the second transfer velocity in a hand-over area having a width; and the pickup velocity and the hand-over velocity are different from each other.

These configurations will be described with reference to the basic conceptual diagram of FIG. 1.

A transfer apparatus 1 provided between a preceding stage C1 and a subsequent stage C2 picks up a workpiece X to a transfer section 3 from the preceding stage C1, and hands over the workpiece X to the subsequent stage C2 after changing the transfer velocity of the workpiece X which has been picked up. Each of the preceding stage C1 and the subsequent stage C2 includes a drum, a conveyer, or any other transfer device, for moving the workpiece X at predetermined transfer velocities, and the configuration of each stage is not limited to any particular configuration.

The workpiece X has a predetermined length with respect to the transfer direction and a predetermined width. The predetermined length is a length that is less than or equal to the longitudinal dimension of the workpiece holding surface of the transfer section 3, and the predetermined width is a width that is less than or equal to the widthwise dimension of the holding surface. With the configuration illustrated in FIG. 1, the workpiece X is transferred in the longitudinal direction in the preceding stage C1, and then the direction thereof is changed in the transfer plane (the revolving plane of the transfer section 3) by means of a direction-changing section 5 provided in the transfer apparatus 1, after which the workpiece X is transferred in the widthwise direction in the subsequent stage C2. Note that the direction of the workpiece X may not be changed, or may be changed from the widthwise direction to the longitudinal direction.

As for the direction-changing section 5, the direction-changing section 5 may have a motor, for example, so that it is capable of turning the transfer section 3. However, in order to allow a rotating member 4 to rotate at a high velocity, it is preferred that the direction-changing section 5 is provided by using a direction-changing cam groove as will be described later. This is because it is then possible to reduce the weight of the rotating member 4. The direction-changing section 5 may alternatively be a rail such as a monorail instead of a direction-changing cam groove 48 as illustrated in FIG. 9. The driving force for turning the transfer section 3 may be supplied from a power source for rotating the rotating member 4.

The transfer apparatus 1 includes at least one transfer section 3 for picking up and holding the workpiece X. The transfer section 3 revolves around a rotation axis 11. In FIG. 1, the transfer section 3 (3a) immediately before picking up the workpiece X from the preceding stage C1 is shown in a solid line, and the transfer section 3 (3b) immediately after picking up the workpiece X is shown in a two-dot chain line. The transfer section 3 (3c) immediately before handing over the workpiece X to the subsequent stage C2 is shown in a solid line, and the transfer section 3 (3d) immediately after handing over the workpiece X is shown in a two-dot chain line.

The transfer section 3 picks up the workpiece X, which is supplied from the preceding stage C1 at a first transfer velocity (transfer velocity V1), in a pickup area adjoining the preceding stage C1 and having a width. At least in this pickup area, the transfer velocity of the transfer plane is maintained at a substantially constant pickup velocity V2. The transfer section 3 being located in the pickup area means that a predetermined point PL of the transfer section 3 is in the pickup area. In the example illustrated in FIG. 1, the predetermined point PL is located at the longitudinal center of the holding surface of the transfer section 3. The pickup velocity V2 is set to be substantially equal to the transfer velocity V1 of the preceding stage C1.

Herein, the pickup area is an area that is defined by an angle R1 about the rotation axis 11 in FIG. 1. The pickup area includes a pickup point SP at which the transfer section 3 comes closest to the preceding stage C1. Where the predetermined point PL is at the longitudinal center of the holding surface of the transfer section 3, it is preferred that the pickup area extends substantially by an angle R1/2 forward and backward with respect to the transfer direction about a line extending between the pickup point SP and the rotation axis 11. However, this may not be the case depending upon the workpiece X to be transferred and the configuration of the transfer section 3. The degree of the angel R1 depends upon the length of the workpiece X along the transfer direction in the vicinity of the pickup point SP.

As the transfer section 3 picks up the workpiece X in the pickup area, the transfer apparatus 1 changes via a velocity-changing section 2 the transfer velocity of the transfer section 3 from the pickup velocity V2 to a hand-over velocity V3. The velocity-changing section 2 is provided on the rotating member 4 rotating about the rotation axis 11, and is capable of reciprocating over a predetermined area of the rotating member 4. For example, the velocity-changing section 2 may have a motor so that it can move with respect to the rotating member 4. However, in order to allow the rotating member 4 to rotate at a high velocity, it is preferred that the velocity-changing section 2 is provided by using a velocity-changing guide that is provided on the rotating member 4 to be eccentric to the rotation axis 11, whereby the circumferential velocity of the transfer section 3 at the revolving surface thereof is changed, as will be described later. This is because it is then possible to reduce the weight of the rotating member 4. The velocity-changing guide may be a groove cam or a rail such as a monorail. Basically, such a velocity-changing guide has a generally circular shape or a generally elliptical shape eccentric to the rotation axis 11, and may include a straight portion and/or a curved portion. By using such a velocity-changing guide, the transfer section 3 can be moved substantially at a constant velocity for a period of time, as will be described later. The driving force for moving the velocity-changing section 2 along the velocity-changing guide may be supplied from a power source for rotating the rotating member 4.

The transfer section 3 releases the workpiece X in a hand-over area adjoining the subsequent stage C2 and having a width. The released workpiece X is handed over to the subsequent stage C2, and transferred at a second transfer velocity (transfer velocity V4). At least in this hand-over area, the transfer velocity of the transfer plane is maintained at a substantially constant hand-over velocity V3. The transfer section 3 being located in the hand-over area means that a predetermined point PS of the transfer section 3 is in the hand-over area. In the example illustrated in FIG. 1, the predetermined point PS is located at the widthwise center of the holding surface of the transfer section 3. The predetermined point PL and the predetermined point PS are different from each other because the transfer section 3 is turned. The hand-over velocity V3 is set to be substantially equal to the transfer velocity V4 of the subsequent stage C2.

The hand-over area is an area that is defined by an angle R2 about the rotation axis in FIG. 1. The hand-over area includes a hand-over point RP at which the transfer section 3 comes closest to the subsequent stage C2. Where the predetermined point PS is at the widthwise center of the holding surface of the transfer section 3, it is preferred that the hand-over area extends substantially by an angle R2/2 forward and backward with respect to the transfer direction about a line extending between the hand-over point RP and the rotation axis 11. However, this may not be the case depending upon the workpiece X to be transferred and the configuration of the transfer section 3. The degree of the angel R2 depends upon the length of the workpiece X along the transfer direction in the vicinity of the hand-over point RP.

As described above, one transfer method and one transfer apparatus of the present invention are configured so that the workpiece X is picked up by the transfer section 3 in a pickup area having a width at the pickup velocity V2 which is substantially equal to the transfer velocity V1 of the preceding stage C1, the transfer velocity of the transfer section 3 having picked up the workpiece X is changed to the hand-over velocity V3, and then the workpiece X is handed over to the subsequent stage C2 in a hand-over area having a width at the hand-over velocity V3 which is substantially equal to the transfer velocity V4 of the subsequent stageC2. Therefore, the transfer pitch of the workpiece X changes as the transfer velocity is changed.

Where the transfer velocity V4 of the subsequent stage C2 is higher than the transfer velocity V1 of the preceding stage C1, a transfer pitch P4 of the workpiece X, which has been handed over to the subsequent stage C2, is wider than a transfer pitch P1 in the preceding stage C1. Conversely, where the transfer velocity V4 of the subsequent stage C2 is lower than the transfer velocity V1 of the preceding stage C1, the transfer pitch P4 of the workpiece X, which has been handed over to the subsequent stage C2, is narrower than the transfer pitch P1 in the preceding stage C1. Then, as the predetermined point PS of the transfer section 3 moves away from the hand-over area, the velocity of the transfer section 3 changes from the hand-over velocity V3 to the pickup velocity V2 before the predetermined point PL of the transfer section 3 enters the pickup area.

In this way, the transfer velocity and the transfer pitch of the workpiece X are changed while the workpiece X is handed over from the preceding stage C1 to the subsequent stage C2, whereby the workpiece X can be efficiently transferred in a manner suitable for the process particulars, the process purposes, etc.

Moreover, a transfer apparatus of the present invention includes a vacuum adjustment section for attracting the workpiece X onto the transfer section 3 by way of vacuum suction at least while the transfer section 3 is in the pickup area, and stopping the vacuum suction so as to release the workpiece X from the transfer section 3 at least while the transfer section 3 is in the hand-over area. With this configuration, even when the workpiece X is by nature soft and unstable, the workpiece X can be smoothly handed over at a high speed without wrinkling the workpiece X.

Furthermore, in the transfer apparatus of the present invention, a holding surface of the transfer section 3 for holding the workpiece X is a convex surface so that the transfer section 3 can reliably pick up and hand over the workpiece X.

It is desirable that at the pickup point SP, the holding surface of the transfer section 3 approaches the workpiece X on the preceding stage C1 in a continuous manner in a direction from the front edge to the rear edge thereof along the transfer direction. For this purpose, the holding surface of the transfer section 3 is provided with an inclination such that the vicinity of the central portion thereof is raised, with respect to the front edge and the rear edge, along the normal line extending from the rotation axis 11 through the vicinity of the central portion of the transfer section 3. More specifically, it is preferred that the holding surface of the transfer section 3 coincides with the revolving plane of the transfer section 3 as the transfer section 3 at the pickup point SP is viewed from a direction along the extension of the rotation axis 11.

Similarly, it is desirable that at the hand-over point RP, the holding surface of the transfer section 3 moves the workpiece X held on the holding surface to continuously approach the transfer plane of the subsequent stage C2 in a direction from the front edge to the rear edge thereof along the transfer direction. For this purpose, the holding surface of the transfer section 3 is provided with an inclination such that the vicinity of the central portion thereof is raised, with respect to the front edge and the rear edge, along the normal line extending from the rotation axis 11 through the vicinity of the central portion of the transfer section 3. More specifically, it is preferred that the holding surface of the transfer section 3 coincides with the revolving plane of the transfer section 3 as the transfer section 3 at the hand-over point RP is viewed from a direction along the extension of the rotation axis 11.

Thus, it is preferred that the shape of the holding surface of the transfer section 3 satisfies the above-described two requirements at the pickup point SP and the hand-over point RP. However, it is not easy to actually produce a curved surface that satisfies such two requirements. Therefore, in the longitudinal direction, only the edges of the holding surface of the transfer section 3 may be formed each as a spherical surface with the normal line mentioned above being the radius thereof.

The holding surface may be formed by using a spherical surface with the normal line mentioned above being the radius thereof, a curved surface approximating to the spherical surface, a flat surface, or a surface made up of a combination thereof. In a case where the holding surface side of the transfer section 3 is made of an elastic material whose shape changes upon application of a pressure, the shape of the transfer section 3 may be any shape other than those described above.

The type of the workpiece X for use in the present invention may include, for example, a product or a semi-finished product of a sanitary napkin, a disposable diaper, disposable underpants, a bandage, other sanitary goods, and similar worn articles in general. Moreover, the form of the workpiece X may include a single sheet or a laminate of sheets layered on one another. The sheet may be liquid absorptive, liquid permeable, liquid semi-permeable, or liquid impermeable. Moreover, the sheet may be woven fabric or non-woven fabric. While the transfer method and the transfer apparatus of the present invention are particularly suitable for transferring the workpieces X of the types and forms as described above, the type and form of the workpieces X are not limited to those described above.

BEST MODE FOR CARRYING OUT THE INVENTION

An embodiment of the present invention will now be described with reference to the drawings.

Figure 2:
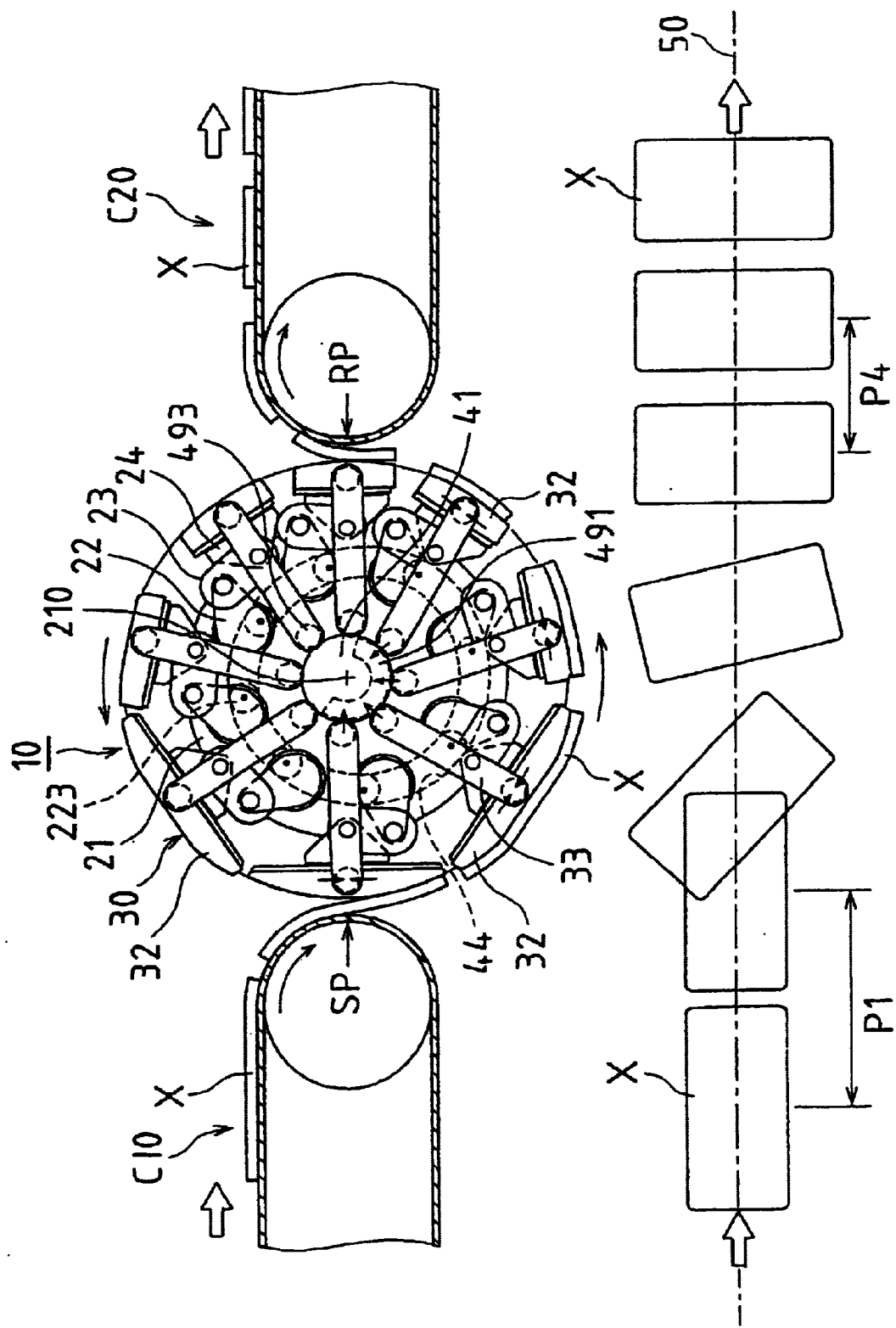
FIG. 2 is a diagram illustrating an example of how a workpiece is transferred by a transfer apparatus according to an embodiment of the present invention.
Figure 3:
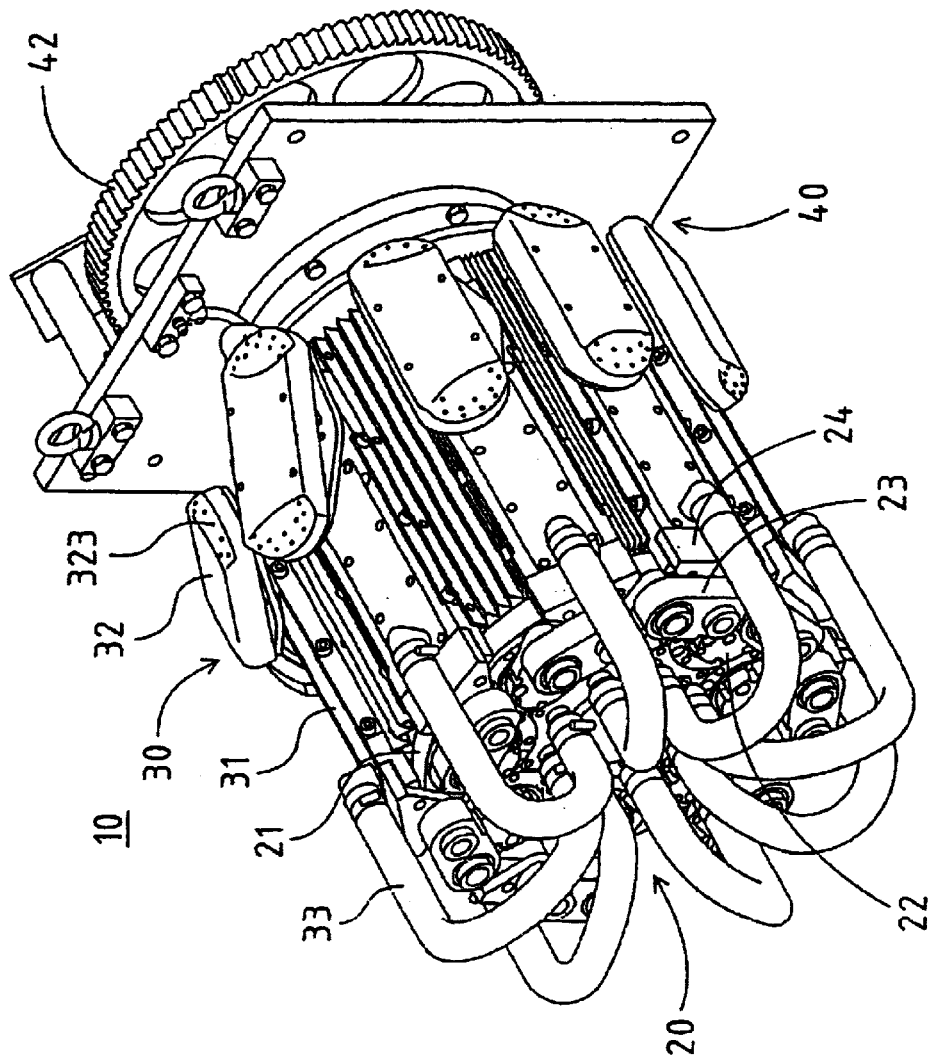
FIG. 3 is a general perspective view illustrating the transfer apparatus.
Figure 4:
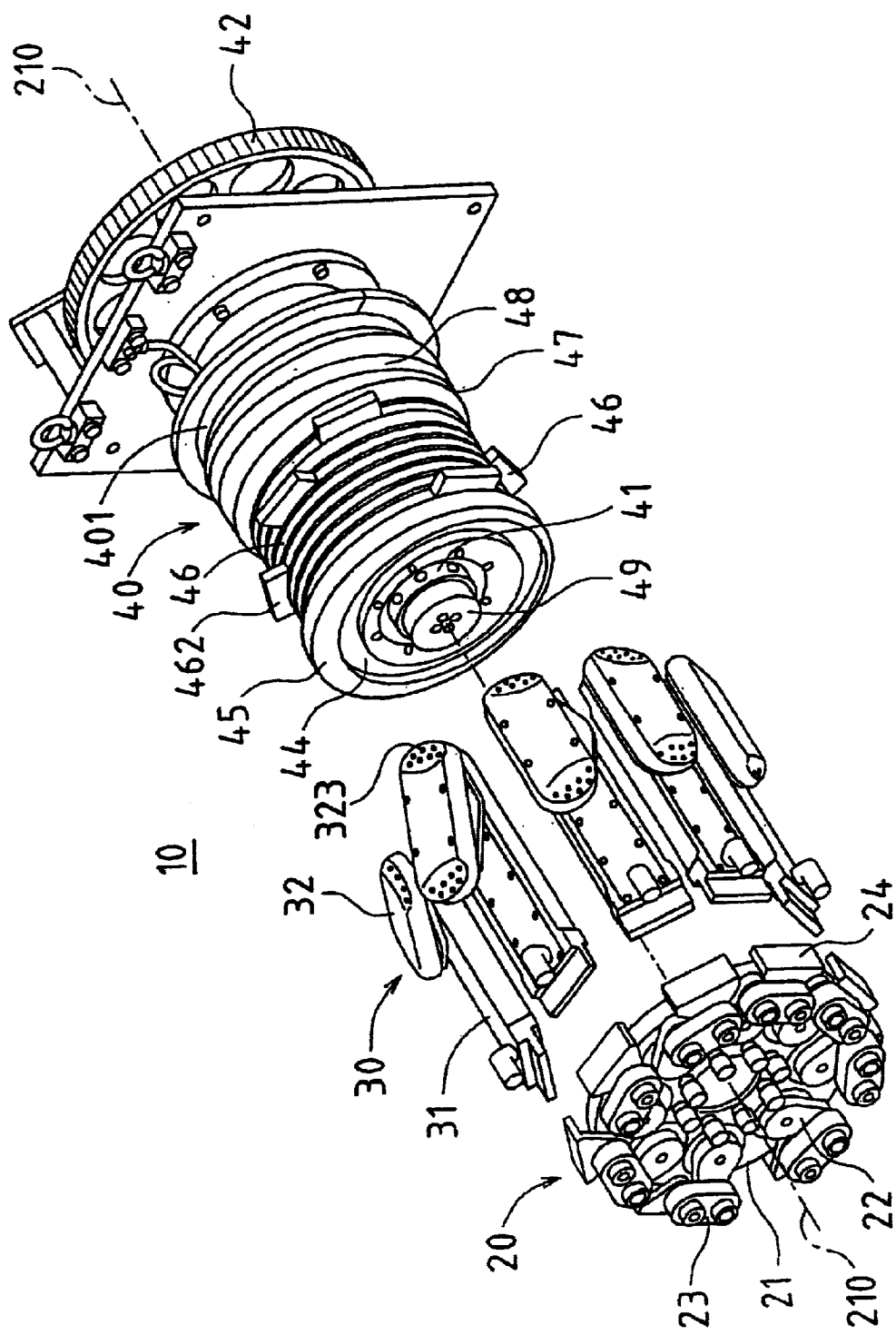
FIG. 4 is an exploded perspective view illustrating a general configuration of the transfer apparatus.

FIG. 2 to FIG. 4 illustrate the operation and general configuration of a transfer apparatus 10 according to an embodiment of the present invention. The transfer apparatus 10 includes a generally cylindrical rotor rotating about a rotation axis 210, and is provided between a preceding stage conveyer C10 and a subsequent stage conveyer C20. Each of the illustrated preceding stage conveyer C10 and subsequent stage conveyer C20 carries a light-weight and soft workpiece X (e.g., sanitary goods such as a sanitary napkin) on an air-permeable transfer belt, and continuously transfers the workpiece X while attracting the workpiece X by way of vacuum suction, etc. The member for attracting the workpiece X is not limited to vacuum suction, but may alternatively be any other suction member such as an electrostatic charge, for example. The transfer member of each of the preceding stage and the subsequent stage may be a drum or any other device instead of a conveyer.

In this embodiment, the workpiece X is transferred in the longitudinal direction on the preceding stage conveyer C10, and is attracted onto the transfer apparatus 10 at the pickup point SP. Then, after the transfer apparatus 10 turns the direction of the workpiece X by about 90° with respect to the transfer direction, the workpiece X is re-mounted onto the subsequent stage conveyer C20 at the hand-over point RP. Then, the workpiece X is transferred on the subsequent stage conveyer C20 in the widthwise direction.

In this embodiment, the transfer velocity of the subsequent stage conveyer C20 is set to be lower than the transfer velocity of the preceding stage conveyer C10, and the subsequent stage transfer pitch P4 at which the workpieces X are arranged in its widthwise direction is narrower than the preceding stage transfer pitch P1 at which the workpieces X are arranged in its longitudinal direction. The transfer apparatus 10 is configured so as to pick up the workpiece X at the predetermined pickup point SP at a high circumferential velocity according to the transfer velocity of the preceding stage conveyer C10, and to hand over the workpiece X at the predetermined hand-over point RP at a low circumferential velocity according to the transfer velocity of the subsequent stage conveyer C20.

As illustrated in FIG. 4, the mechanism of the transfer apparatus 10 can be generally divided into the following sections: a velocity-changing section 20 having a generally disc-shaped driving wheel 21; at least one (eight in this example) revolving section 30 being attached to the driving wheel 21 along the periphery thereof and revolving with the driving wheel 21; and a generally cylindrical base body section 40 for rotatably/revolvably supporting the velocity-changing section 20 and the revolving sections 30.

Figure 5:
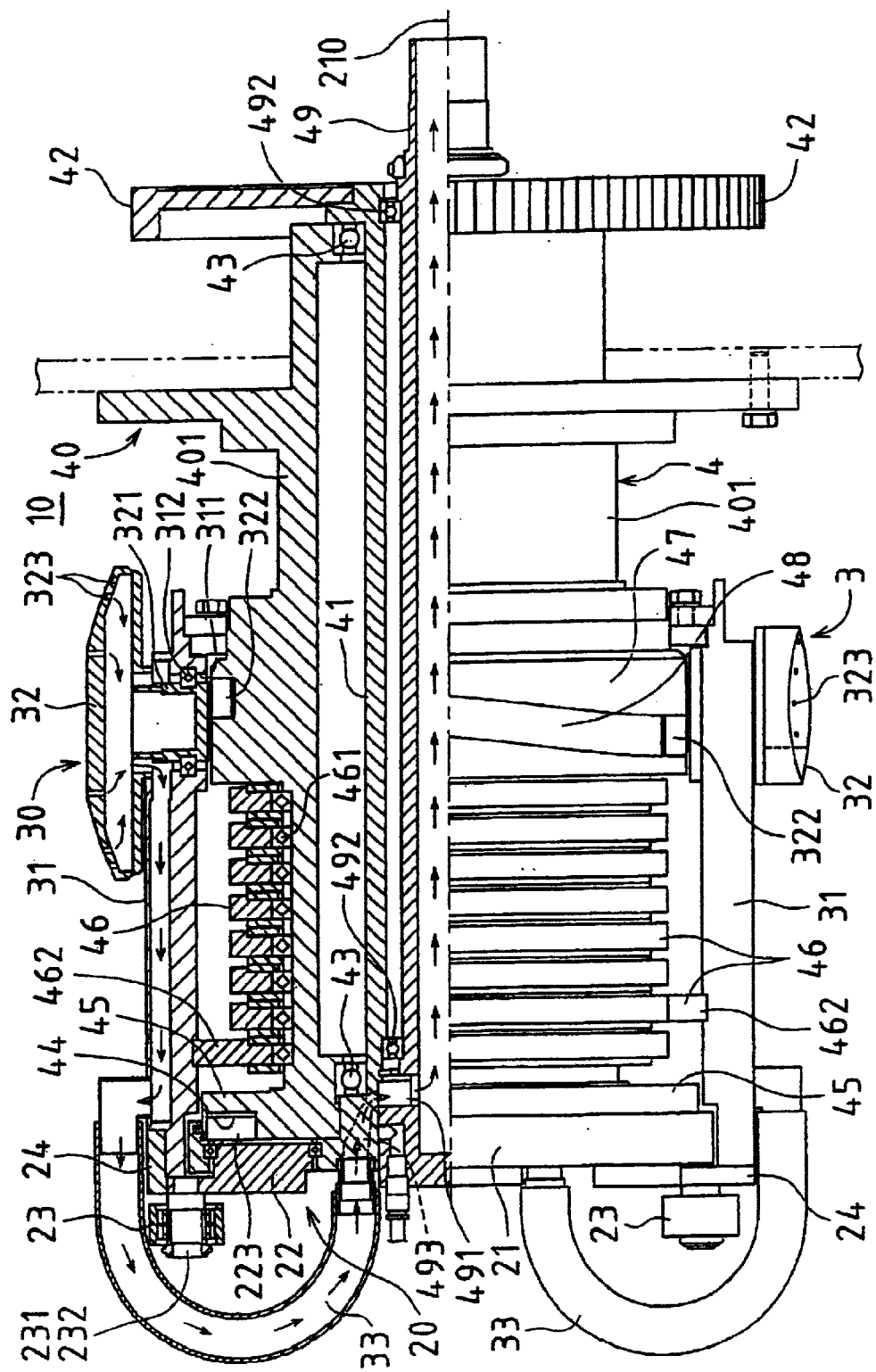
FIG. 5 is a partially-cross-sectional side view illustrating a side view of the transfer apparatus as viewed from a direction perpendicular to the rotation axis thereof, while also illustrating a cross section thereof taken along a plane including the rotation axis.

The velocity-changing section 20 includes the driving wheel 21, crank arms 22, link levers 23, and linking blocks 24. As illustrated in FIG. 5, the driving wheel 21 is linked to one end of a driving shaft 41, which is inserted through the center of the base body section 40. A driving gear 42 is attached to the other end of the driving shaft 41. The driving shaft 41 and the driving wheel 21 rotate at a constant velocity about the rotation axis 210 while obtaining a driving force from a motor (not shown), etc., via the driving gear 42.

Figure 6:
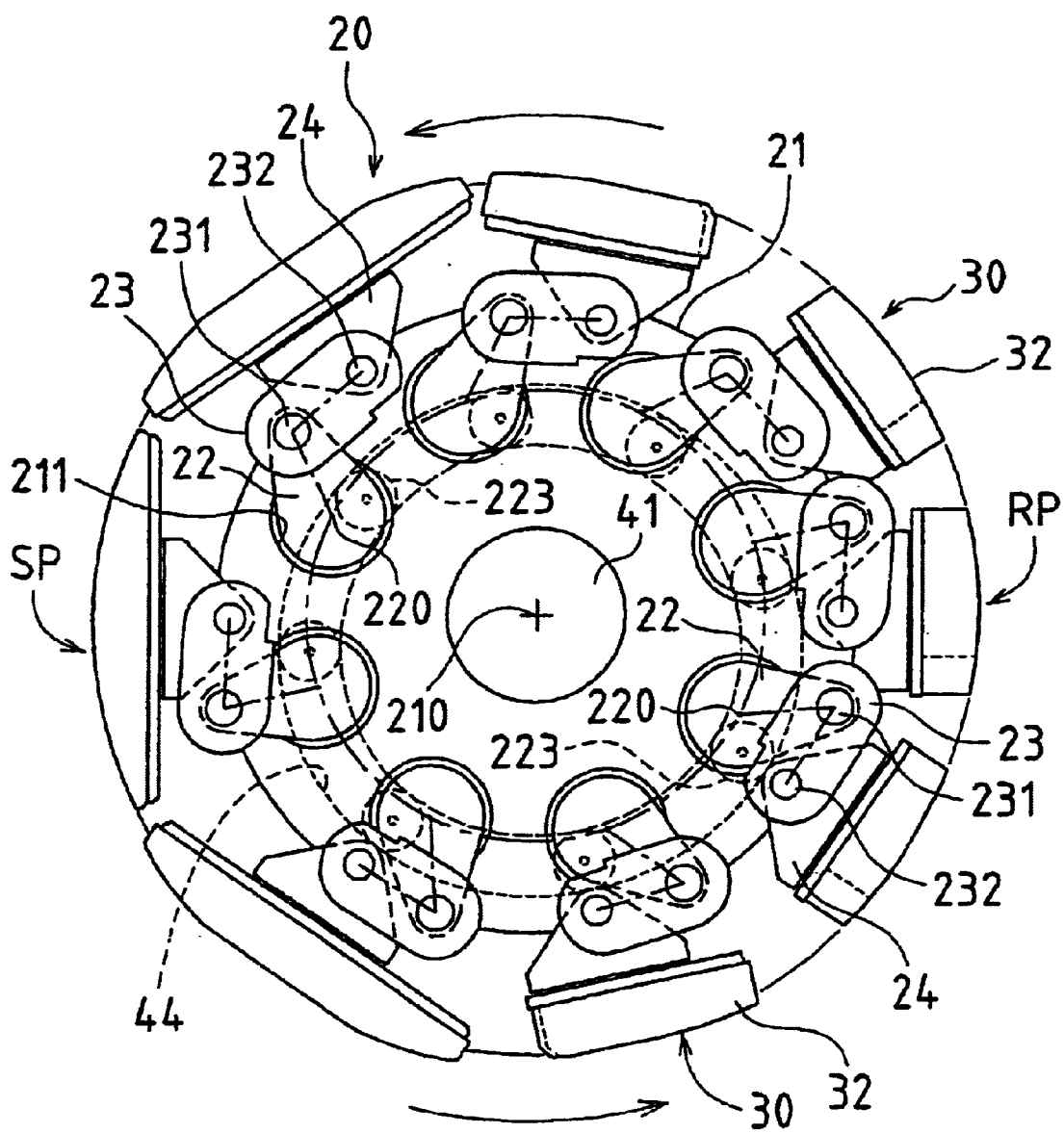
FIG. 6 is a front view illustrating an operation of a link mechanism for accelerating/decelerating the velocity of a revolving section.
Figure 7:
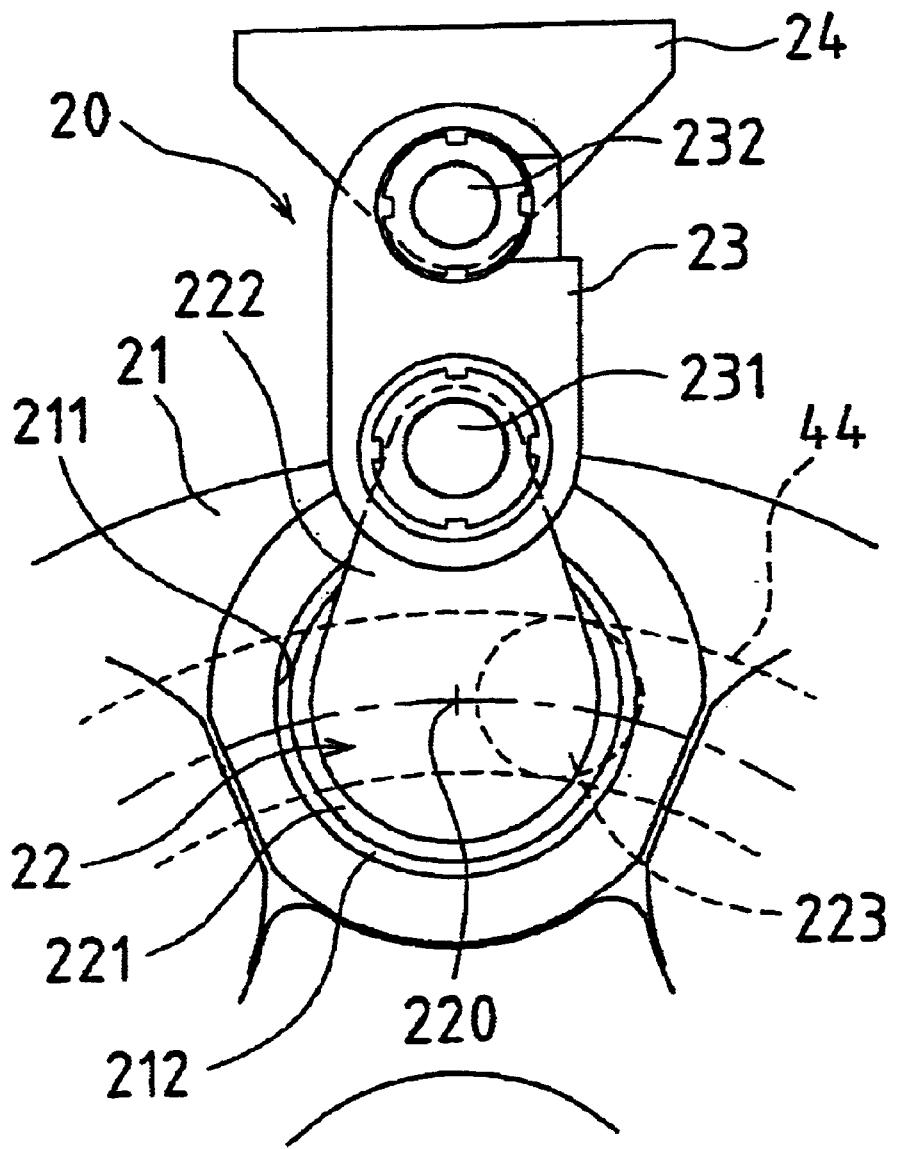
FIG. 7 is a partial front view illustrating the link mechanism as viewed from a direction along the extension of the rotation axis.
Figure 8:
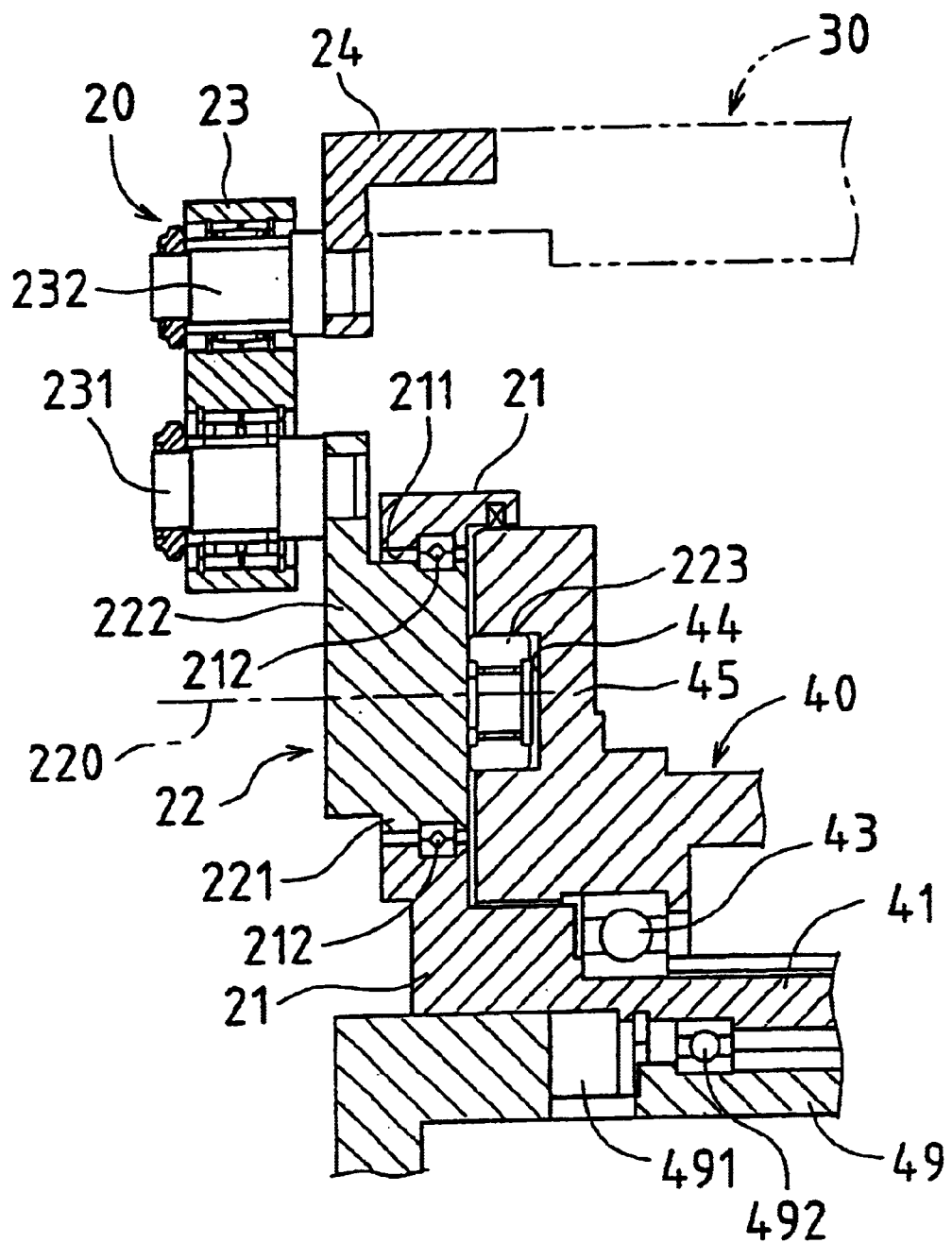
FIG. 8 is a partial cross-sectional view illustrating a cross section of the link mechanism taken along a plane including the rotation axis.

As illustrated in FIG. 6 to FIG. 8, the same number of crank arms 22 as the revolving sections 30 are attached to the driving wheel 21 near the periphery thereof and are disposed at regular intervals. Each crank arm 22 includes a disc-shaped substrate section 221, an arm section 222 extending from the surface of the substrate section 221 in the direction away from the substrate section 221, and a velocity-changing cam roller 223 protruding on the reverse side of the substrate section 221. The substrate section 221 is attached via an annular bearing 212 to a crank arm support hole 211 formed in a circular shape in the driving wheel 21. Thus, the crank arms 22 are held with respect to the driving wheel 21 so that they can be turned independently of one another. The velocity-changing cam roller 223 is provided at a position spaced apart from a pivot center 220 of the crank arm 22 by a distance, and moves along a velocity-changing cam groove 44 to be described later.

The arm section 222 of each crank arm 22 is pivotally linked to one end of the link lever 23 via a pin linking section 231. The other end of the link lever 23 is pivotally linked to the linking block 24 via a pin linking section 232. One end of the revolving section 30 is fixed to the linking block 24.

The pin linking section 231 may be any linking structure as long as it pivotally links the crank arm 22 and the link lever 23 to each other. Similarly, the pin linking section 232 may be any linking structure as long as it pivotally links the link lever 23 and the linking block 24 to each other.

As illustrated in FIG. 4 to FIG. 5, the base body section 40 includes a generally cylindrical casing 401, the driving shaft 41 and the driving gear 42 described above, a flange 45 formed at one end of the casing 401, lock plates 46 attached to the casing 401 along the periphery thereof, a cylindrical cam 47 provided along the periphery of the casing 401, a vacuum shaft 49 inserted through the driving shaft 41, etc. The casing 401, the cylindrical cam 47, the driving shaft 41, the driving gear 42 and the vacuum shaft 49 are coaxial with the rotation axis 210.

The driving shaft 41 has a hollow cylindrical shape and is rotatably attached to the casing 401 via a bearing 43. The vacuum shaft 49 inserted through the driving shaft 41 is rotatably held with respect to the driving shaft 41 via a bearing 492. Therefore, even when the driving shaft 41 rotates, the casing 401 and the vacuum shaft 49 do not rotate.

The flange 45 is provided with the velocity-changing cam groove 44. The velocity-changing cam roller 223 of the crank arm 22 in the velocity-changing section 20 described above is placed in the velocity-changing cam groove 44, and is held so that it can move along the velocity-changing cam groove 44. Thus, the velocity-changing cam groove 44 serves as a velocity-changing guide that restricts the movement of the velocity-changing cam roller 223. While it is preferred that the shape of the velocity-changing cam groove 44 is a generally circular shape or a generally elliptical shape, it may alternatively be composed of a group of linear segments and/or non-linear segments. In this embodiment, the velocity-changing cam groove 44 is formed in a generally elliptical shape that is eccentric to the rotation axis 210, as illustrated in FIG. 6.

The direction-changing cam groove 48 is provided around the periphery of the cylindrical cam 47. The direction-changing cam groove 48 is formed so as to run all the way around the side surface of the cylindrical cam 47 while being displaced in the direction of the generatrix of the cylindrical cam 47 (the direction parallel to the rotation axis 210). The cylindrical cam 47 serves as a direction-changing guide that restricts the movement of a direction-changing cam roller 322 to be described later.

Each revolving section 30 includes an elongate, flat, and box-shaped drive box 31, and an attracting member 32 pivotally held at one end of the drive box 31. The drive box 31 is linked to the link lever 23 via the linking block 24, and is linked to the lock plate 46 attached to the base body section 40 along the periphery thereof, as illustrated in FIG. 5. The lock plates 46 are generally annular members, attached to the casing 401 of the base body section 40 via bearings 461, and held so that they can rotate around the casing 40 independently of one another. Each lock plate 46 is provided with an arm 462 protruding from a position of the lock plate 46 along its circumference, and the drive box 31 is linked to the arm 462. Therefore, the drive box 31 revolves around the base body section 40 being entailed by the rotation of the driving wheel 21, while keeping a constant distance from the rotation axis 210 with the longitudinal direction thereof being parallel to the rotation axis 210.

Figure 1:
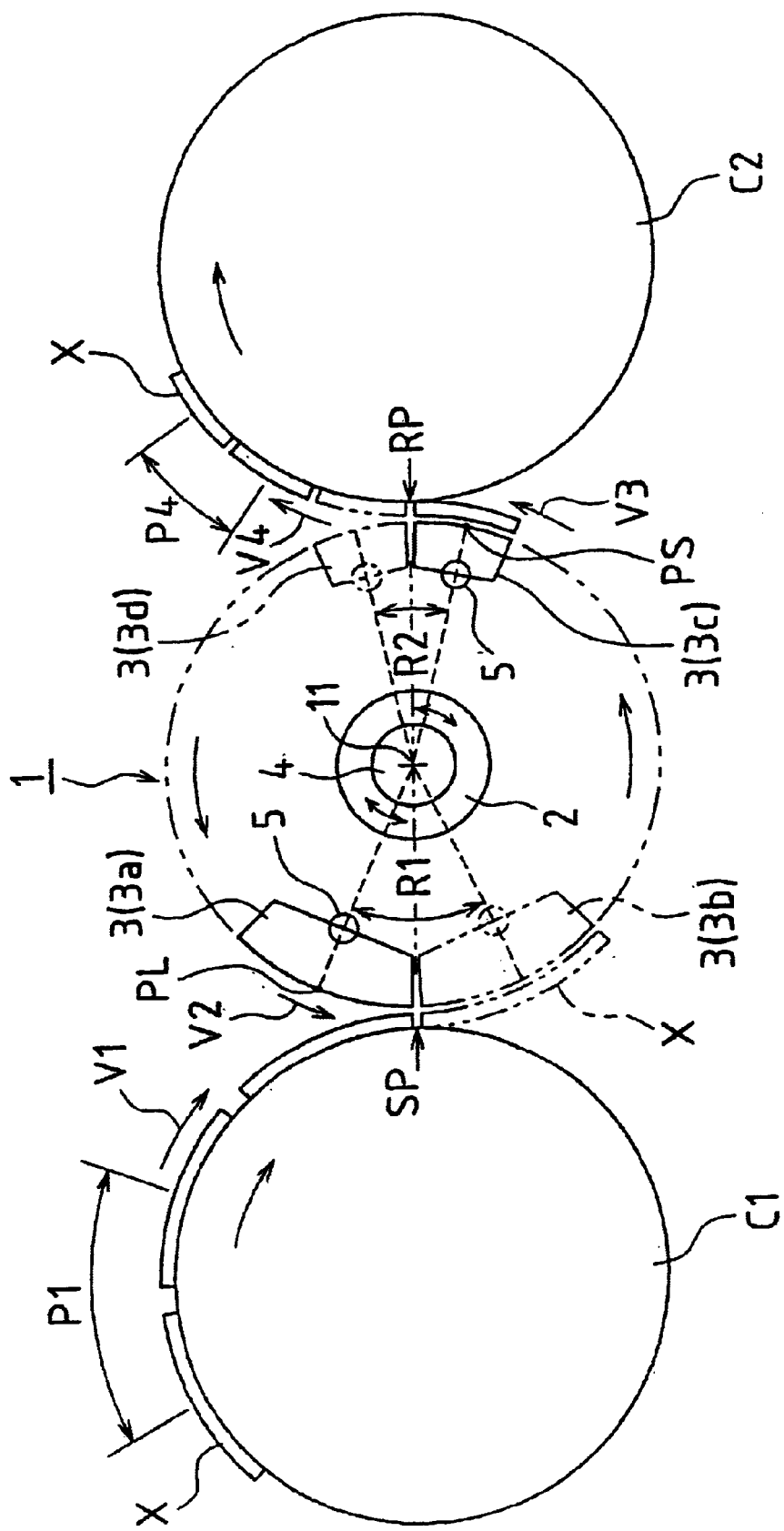
FIG. 1 is a diagram illustrating the basic concept of a transfer method and a transfer apparatus of the present invention.
Figure 9:
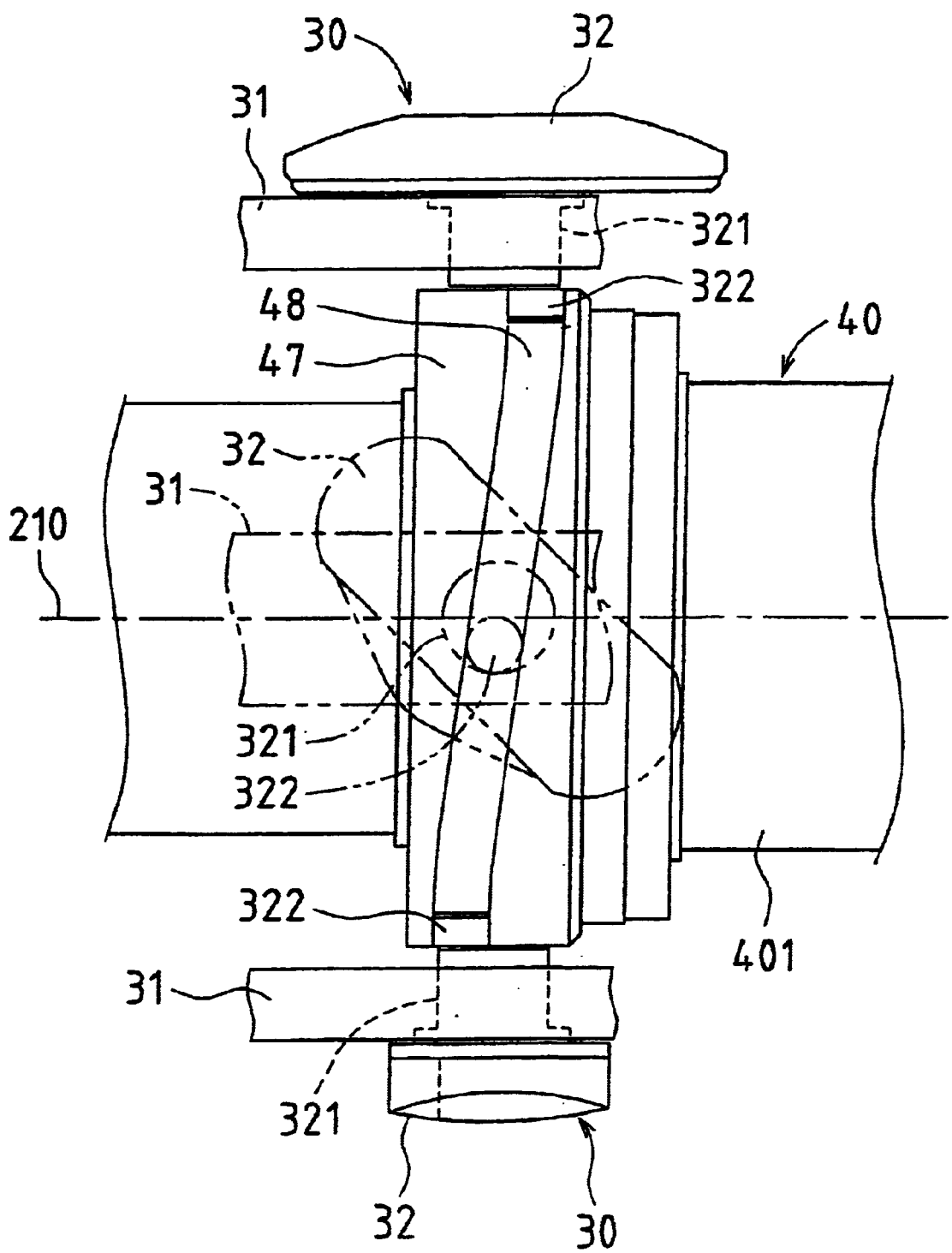
FIG. 9 is a partial side view illustrating a cylindrical cam mechanism for turning an attracting member of a revolving section.

The attracting member 32 is a member for attracting/releasing the workpiece X, and corresponds to the transfer section 3 in the basic concept of the present invention illustrated in FIG. 1. The surface of the attracting member 32 serves as the holding surface for the workpiece X. The attracting member 32 has a cylindrical pivot shaft 321 generally at the center thereof. The pivot shaft 321 is pivotally held, via a bearing 312, by a cylindrical support section 311 provided in the drive box 31. The pivot shaft 321 is held in a direction perpendicular to the revolving plane of the revolving drive box 31, i.e., a direction toward the rotation axis 210. Moreover, the attracting member 32 is provided with the direction-changing cam roller 322. The direction-changing cam roller 322 is provided so as to protrude on the side of the base body section 40 at a position spaced apart from the pivot center of the pivot shaft 321 by a distance. The direction-changing cam roller 322 moves along the direction-changing cam groove 48 formed in the cylindrical cam 47 of the base body section 40, as illustrated in FIG. 9. The direction-changing cam groove 48 is formed so as to run all the way around the side surface of the cylindrical cam 47 while being displaced in the direction of the generatrix of the cylindrical cam 47. Therefore, the attracting member 32 moves with periodic pivoting within a angle range according to the position of the direction-changing cam roller 322 along the direction-changing cam groove 48. As illustrated in FIG. 2, in this embodiment, the attracting member 32 has its longitudinal direction aligned with the revolving direction at the pickup point SP, and the attracting member 32 is turned by about 90° while the revolving section 30 moves halfway around, so that at the hand-over point RP, the widthwise direction thereof is aligned with the revolving direction.

The drive box 31 and the attracting member 32 are hollow and are communicated to each other as illustrated in FIG. 5. The surface of the attracting member 32 is provided with a plurality of small apertures 323 that reach the inside of the attracting member 32. It is preferred that the small apertures 323 are provided at least in the vicinity of the front edge of the holding surface of the attracting member 32 in the revolving direction. This is because it is easier to prevent the workpiece X from being wrinkled upon picking up the workpiece X, when the workpiece X starts to be attracted by a portion of the holding surface of the attracting member 32 that first reaches the pickup point SP.

A hose 33 curved in a U shape is connected to one end of each of the drive boxes 31. The hose 33 is connected to a vacuum communication aperture 493 formed in the vicinity of the junction between the driving wheel 21 and the driving shaft 41.

The vacuum communication aperture 493 meets a vacuum adjustment port 491 provided at one end of the vacuum shaft 49. The vacuum adjustment port 491 is formed by, for example, providing an opening in the vacuum shaft 49 having a cylindrical shape at a position along its circumference. Thus, the vacuum communication aperture 493, which rotates along with the driving wheel 21, is communicated to, and disconnected from, the vacuum adjustment port 491 depending upon its position in rotation. When the vacuum communication aperture 493 is communicated to the vacuum adjustment port 491, the air is sucked from the other end of the vacuum shaft 49, as indicated by arrows in FIG. 5, to depressurize the inside of the suction path extending from the hose 33 to the attracting member 32 via the drive box 31, thereby attracting the workpiece X onto the attracting member 32. Conversely, when the vacuum communication aperture 493 and the vacuum adjustment port 491 are disconnected from each other, the internal pressure of the suction path is recovered to about the atmospheric pressure, thereby releasing the workpiece X from the attracting member 32. In this embodiment, the vacuum adjustment port 491 is formed so that the suction path is established when the attracting member 32 comes close to the pickup point SP and disconnected when the attracting member 32 comes close to the hand-over point RP, as illustrated in FIG. 2. With the vacuum adjustment section having the vacuum adjustment port 491 as described above, the timing of attracting and releasing the workpiece X is controlled.

The specific manner of controlling the timing of establishing or disconnecting the suction path may be modified as necessary as long as the path is established at least at the pickup point SP and disconnected at least at the hand-over point RP.

With the transfer apparatus 10 of this embodiment, the transfer velocity is changed as follows.

As illustrated in FIG. 6, the driving wheel 21 is provided with a plurality of crank arms 22, which are disposed at regular intervals (regular angular intervals with respect to the rotation axis 210). The interval between the crank arms 22 is constant, and the pivot center 220 of each of the crank arms 22 rotates at the same angular velocity as the driving wheel 21.

However, the velocity-changing cam roller 223 is provided for each crank arm 22 at a position spaced apart from the pivot center 220 thereof, and the velocity-changing cam roller 223 moves along the velocity-changing cam groove 44 formed in the flange 45 of the base body section 40. The velocity-changing cam groove 44 is formed to be eccentric to the center of the driving wheel 21 (the rotation axis 210), and does not move. Therefore, the distance from the rotation axis 210 to the velocity-changing cam roller 223 periodically increases/decreases depending upon the positions of the velocity-changing cam roller 223 and the velocity-changing cam groove 44. Thus, the crank arm 22 periodically pivots within a angle range, whereby the tip of the crank arm 22 periodically swings. Specifically, the tip of the crank arm 22 is displaced forwardly in the transfer direction with respect to the pivot center 220 of the crank arm 22 in the first range (generally the lower half in FIG. 6), and backwardly in the second range (generally the upper half in FIG. 6). Then, the link lever 23 pin-linked to the tip of the crank arm 22 and the linking block 24 pin-linked to the link lever 23 are also displaced forwardly or backwardly being entailed by the swinging of the tip of the crank arm 22. Moreover, since the distance between the pivot center 220 of the crank arm 22 and the linking block 24 changes as the crank arm 22 swings, the interval between adjacent linking blocks 24 also changes. As a result, the angular velocity of the revolving section 30 linked to the linking block 24, and the interval thereof with respect to the adjacent revolving sections 30, change.

Since each revolving section 30 is individually linked to the lock plate 46 (see FIG. 4, FIG. 5), the distance from the rotation axis 210 to each revolving section 30 is always constant, and the orientation of the revolving section 30 with respect to the transfer plane is also held constant.

While the revolving section 30 smoothly revolves around the base body section 40, the revolving section 30 is accelerated in an accelerating area so that the revolving section 30 is at a pickup velocity in the pickup area where it picks up the workpiece X, thereby increasing the interval between adjacent transfer sections 30, and the revolving section 30 is decelerated in a decelerating area so that the revolving section 30 is at a hand-over velocity in the hand-over area where it hands over the workpiece X, thereby decreasing the interval between adjacent transfer sections 30. Thus, the workpiece X is picked up in the pickup area from the preceding stage conveyer C10 whose transfer velocity is high, and the workpiece X is handed over in the hand-over area to the subsequent stage conveyer C20 whose transfer velocity is low. The arrangement of the pickup area, the decelerating area, the hand-over area and the accelerating area may be adjusted as necessary by changing the shape of the velocity-changing cam groove 44, the position of the velocity-changing cam roller 223 in the crank arm 22, etc.

As described above, the transfer apparatus 10 of this embodiment is characterized in that: the revolving section 30 is rotatably held with respect to the rotation axis 210 while it is held at a constant distance from the rotation axis 210; the crank arm 22 pivotally held with respect to the driving wheel 21 and the link lever 23 whose one end is pin-linked to the tip of the crank arm 22 are provided in the vicinity of the periphery of the driving wheel 21, the other end of the link lever 23 being pin-linked to the revolving section 30; the crank arm 22 is provided with the velocity-changing cam roller 223 protruding therefrom at a position spaced apart from the pivot center 220 thereof; the velocity-changing cam roller 223 moves along the velocity-changing cam groove 44 formed to be eccentric to the driving wheel 21, whereby the tip of the crank arm 22 swings with respect to the driving wheel 21 during one complete rotation of the driving wheel 21; and, as a result, the angular velocity of the revolving section 30 linked to the crank arm 22 via the link lever 23 periodically increases/decreases with respect to the angular velocity of the driving wheel 21.

By changing the circumferential velocity of the revolving section 30 in the pickup area (the pickup velocity) from the circumferential velocity of the revolving section 30 in the hand-over area (the hand-over velocity) as described above, the transfer velocity can be smoothly decreased/increased between the preceding stage and the subsequent stage having different transfer velocities. Therefore, even when the workpiece X is a soft and light-weight item, the workpiece X can be handed over appropriately, continuously, and at a high velocity, thereby contributing to an increase in the efficiency of the manufacturing process. Moreover, since a driving force that gives the driving wheel 21 a constant-velocity rotation is sufficient as the driving force for driving the transfer apparatus 10, it is not necessary to control the driving force with complicated controller.

Furthermore, in addition to the above-described configuration, the transfer apparatus 10 is characterized in that: the revolving section 30 is provided with the attracting member 32 capable of pivoting in the transfer plane; the attracting member 32 is provided with the direction-changing cam roller 322 protruding therefrom at a position spaced apart from the pivot center thereof; the cylindrical cam 47 coaxial with the rotation axis 210 is provided inside the locus of revolution of the revolving section 30; the direction-changing cam groove 48 is formed around the side surface of the cylindrical cam 47 while being displaced in the direction of the generatrix thereof; and the direction-changing cam roller 322 is guided along the direction-changing cam groove 48, whereby the direction of the attracting member 32 with respect to the transfer direction periodically changes depending upon the position of the revolving section 30.

With such a configuration, it is possible to pivot the attracting member 32 in the transfer plane and to change the direction of the workpiece X with respect to the transfer direction while the workpiece X is handed over from the preceding stage to the subsequent stage. Thus, it is possible to transfer the workpiece X in a direction suitable for the process particulars and/or the process purposes of the preceding and subsequent stages.

The above embodiment has been described with respect to the particular manner of transfer, in which the workpiece X is transferred along the longitudinal direction on the preceding stage conveyer C10 where the velocity is high, and then the workpiece X is decelerated and the direction thereof is changed by the transfer apparatus 10, after which it is transferred along the widthwise direction on the subsequent stage conveyer C20 where the velocity is low. However, the present invention is not limited to this, and the transfer apparatus 10 can be also used to address other situations where, for example, the velocity of the preceding stage conveyer C10 is low and the velocity of the subsequent stage conveyer C20 is high, by reversing the position and timing of accelerating/decelerating the revolving section 30 from that described above. In such a case, a more complicated shape than a generally circular shape or a generally elliptical shape may be employed for the velocity-changing cam groove 44 so as to achieve more complicated accelerating/decelerating timings. Moreover, it is optional to change the direction of the workpiece X with respect to the transfer direction, and the angle by which the workpiece X is turned is not limited to 90°, but one may freely set it by changing the shape of the cylindrical cam 47. Moreover, the present invention can be applied to apparatuses in which the unit for attracting/releasing the workpiece x is provided by using a mechanism other than a vacuum mechanism.

Where the attracting member 32 illustrated in FIG. 6 and FIG. 9 is formed in a shape indicated by a broken line, not a solid line, the workpiece X can be handed over to the subsequent stage while it is shifted from a center line 50 of the transfer direction illustrated in FIG. 2. In the attracting member 32 having a shape indicated by the broken line, the pivot center of the attracting member 32 and the center of the holding surface thereof are offset from each other, thereby shifting the workpiece X from the center line 50 of the transfer direction only to one side. Note however that the workpieces X may be placed in a staggered arrangement with respect to the center line 50, for example, by individually changing the shape of the holding surface of the attracting member 32 and/or the positional relationship between the holding surface and the object-turning cam roller 322.

Industrial Applicability

With the transfer method or the transfer apparatus of the present invention, a workpiece having a predetermined length can be picked up in a pickup area at a pickup velocity that is substantially equal to the transfer velocity of the preceding stage, and can be handed over in a hand-over area to the subsequent stage at a hand-over velocity that is substantially equal to the transfer velocity of the subsequent stage. Therefore, it is unlikely that the workpiece is wrinkled or elongated more than necessary upon picking up and releasing the workpiece. Particularly, the present invention is such that the transfer velocity of the workpiece does not substantially change between a point in time immediately before and a point in time immediately after picking up and releasing the workpiece, and thus the present invention is suitable for transfer at a high speed.

Moreover, with the transfer method or the transfer apparatus of the present invention, since the pickup velocity and the hand-over velocity are different from each other, the transfer pitch of the workpieces can be changed. Therefore, in a case where, for example, a continuous material is cut into workpieces of a predetermined length, while there is substantially no spacing between workpieces immediately after the cutting, the transfer pitch of the workpieces can be increased by handing over the workpieces to another stage by using the transfer method or the transfer apparatus of the present invention. In a case where, for example, a web having an adhesive member is transferred in the subsequent stage, workpieces can be arranged on the web at an intended interval.

Thus, the present invention makes it possible to manufacture sanitary goods or other worn articles, for example, at a high speed. Moreover, the present invention makes it possible to prevent troubles that can be encountered while transferring workpieces and/or to reduce the possible loss of the material being processed during a transfer step, thereby improving the efficiency in transferring and processing the workpieces.

What is claimed is:

1. A transfer method for transferring a workpiece from a preceding stage to a subsequent stage by using a transfer apparatus comprising at least one transfer section capable of revolving around a rotation axis, the method comprising:
    a pickup step, wherein in order for the transfer section to pick up the workpiece transferred by the preceding stage at a first transfer velocity, the transfer section moves at a pickup velocity substantially equal to the first transfer velocity in a pickup area;
    a velocity-changing step of changing the transfer velocity of the transfer section while the transfer section is holding the workpiece which has been picked up, using a velcoity-changing guide that is eccentric to the rotation axis and does not move around the rotation axis;
    a direction-changing step of changing a direction of the workpiece by pivoting the transfer section about an axis transverse the rotation axis using a direction-changing guide that runs along a path around the curved surface of a nonrotatable cylinder that is coaxial with the axis of rotation, the path of the direction-changing guide being displaced in a direction parallel to the rotation axis to effect the pivoting of the transfer section; and
    a hand-over step, wherein in order to transfer the workpiece at a second transfer velocity by the subsequent stage, the transfer section moves at a hand-over velocity substantially equal to the second transfer velocity in a hand-over area,
    wherein the pickup velocity and the hand-over velocity are different from each other.

2. A transfer method according to claim 1, wherein the direction-changing step includes changing a direction of the workpiece by pivoting the transfer section in a transfer plane between the pickup step and the hand-over step.

3. A transfer method according to claim 1, wherein where the hand-over velocity is higher than the pickup velocity, a transfer pitch of workpieces in the hand-over area is increased to be greater than a transfer pitch of the workpieces in the pickup area.

4. A transfer method according to claim 1, wherein where the hand-over velocity is lower than the pickup velocity, a transfer pitch of workpieces in the hand-over area is decreased to be less than a transfer pitch of the workpieces in the pickup area.

5. A transfer method according to claim 1, wherein the workpiece is one of a product and a semi-finished product of sanitary goods or a similar worn article, a single sheet, and a laminate of sheets.

6. A transfer apparatus, comprising at least one transfer section capable of revolving around a rotation axis, a direction-changing section for changing a direction of the workpiece by pivoting the transfer section about an axis transverse the rotation axis, the direction-changing section including a direction-changing guide that runs along a path around the curved surface of a nonrotatable cylinder that is coaxial with the rotation axis, that path of the direction-changing guide being displaced in a direction parallel to the rotation axis to effect the pivoting of the transfer section, and a velocity-changing section for changing a transfer velocity of the transfer section, the vilocity-changing section including a velocity-changing guide that is eccentric to the rotation axis and does not move around the rotation axis wherein:
    in order for the transfer section to pick up a workpiece transferred at a first transfer velocity, the transfer section holds the workpiece while moving at a pickup velocity substantially equal to the first transfer velocity in a pickup area having a width;
    the velocity-changing section changes the transfer velocity of the transfer section holding the workpiece;
    in order to transfer the workpiece at a second transfer velocity outside the transfer apparatus, the transfer section moves at a hand-over velocity substantially equal to the second transfer velocity in a hand-over area having a width; and
    the pickup velocity and the hand-over velocity are different from each other.

7. A transfer apparatus according to claim 6, comprising a direction-changing section for changing a direction of the workpiece by pivoting the transfer section in a transfer plane while the transfer section moves from the pickup area to the hand-over area.

8. A transfer apparatus according to claim 6, comprising a vacuum adjustment section for attracting the workpiece onto the transfer section by way of vacuum suction at least while the transfer section is in the pickup area, and stopping the vacuum suction so as to release the workpiece from the transfer section at least while the transfer section is in the hand-over area.

9. A transfer apparatus according to claim 8, wherein the vacuum adjustment section has a vacuum adjustment port,
    the vacuum adjustment port is formed by providing an opening in a vacuum shaft,
    a vacuum communication aperture is communicated to, and disconnected from, the vacuum adjustment port depending upon its position in rotation, and
    when the vacuum communication aperture is communicated to the vacuum adjustment port, a vacuum draws air from a drive box at one end of the vacuum shaft.

10. A transfer apparatus according to claim 9, wherein one end of a hose is connected to the drive box, and the other end of the hose is connected to the vacuum communication aperture.

11. A transfer apparatus according to claim 10, wherein the hose is curved in a U shape.

12. A transfer apparatus according to claim 6, wherein a holding surface of the transfer section for holding the workpiece is provided with an inclination such that a vicinity of a central portion of the holding surface is higher than a front edge and a rear edge of the holding surface with respect to a transfer direction, whereby in the hand-over area, the holding surface moves the workpiece to approach to a portion of the subsequent stage where the subsequent stage receives the workpiece being handed over in a direction from the front edge to the rear edge thereof along the transfer direction.

13. A transfer apparatus according to claim 6, wherein the velocity-changing guide is a groove cam.

14. A transfer apparatus according to claim 6, wherein the velocity-changing guide is a rail.

15. A transfer apparatus according to claim 6, wherein the direction-changing guide is a rail.

16. A transfer apparatus according to claim 6, wherein the direction-changing guide is a rail.

17. A transfer apparatus according to claim 6, wherein a holding surface of the transfer section for holding the workpiece is a convex surface.

18. A transfer apparatus according to claim 6, wherein a holding surface of the transfer section for holding the workpiece is provided with an inclination surface that a vicinity of a central portion of the holding surface is higher than a front edge and a rear edge of the holding surface with respect to a transfer direction, whereby in the pickup area, the holding surface approaches the workpiece from preceding stage in a direction from the front edge thereof along the transfer direction.

* * * * *